United States Patent
Stuermer et al.

(10) Patent No.: US 9,057,138 B2
(45) Date of Patent: Jun. 16, 2015

(54) ENERGY SUPPLY SYSTEM AND OPERATING METHOD

(75) Inventors: Bernd Stuermer, Stuttgart (DE); Volkmar Frick, Tuebingen (DE); Michael Specht, Waldenbuch (DE); Michael Sterner, Kassel (DE); Berthold Hahn, Kassel (DE); Ulrich Zuberbuehler, Stuttgart (DE)

(73) Assignee: Zentrum fuer Sonnenenergie- und Wasserstoff-Forschung Baden-Wuerttemberg, Stuttgart (DE)

( * ) Notice: Subject to any disclaimer, the term of this patent is extended or adjusted under 35 U.S.C. 154(b) by 153 days.

(21) Appl. No.: 13/263,940
(22) PCT Filed: Apr. 9, 2010
(86) PCT No.: PCT/EP2010/054710
§ 371 (c)(1), (2), (4) Date: Dec. 6, 2011
(87) PCT Pub. No.: WO2010/115983
PCT Pub. Date: Oct. 14, 2010

(65) Prior Publication Data
US 2012/0091730 A1    Apr. 19, 2012

(30) Foreign Application Priority Data
Apr. 9, 2009   (DE) .......................... 10 2009 018 126

(51) Int. Cl.
*F03B 13/00*   (2006.01)
*C25B 1/04*    (2006.01)
(Continued)

(52) U.S. Cl.
CPC *C25B 1/04* (2013.01); *C12M 21/04* (2013.01); *C12M 43/08* (2013.01); *Y02E 60/366* (2013.01); *C10L 3/08* (2013.01); *C12M 43/00* (2013.01); *Y02E 60/324* (2013.01)

(58) Field of Classification Search
CPC ........ Y02E 10/46; Y02E 20/16; Y02E 60/366
USPC ....................................................... 290/1 R
See application file for complete search history.

(56) References Cited

U.S. PATENT DOCUMENTS 5,255,504 A * 10/1993 Hodrien et al. .................. 60/781
5,512,787 A *  4/1996 Dederick ....................... 290/4 R
(Continued)

FOREIGN PATENT DOCUMENTS

DE           43 32 789 A1    3/1995
DE      10 2004 030 717 A1   1/2006
(Continued)

OTHER PUBLICATIONS

English translation of the International Preliminary Report on Patentability, PCT/IB/338, PCT/IB/373 and PCT/ISA/237. (seven (7) pages).

(Continued)

*Primary Examiner* — Tulsidas C Patel
*Assistant Examiner* — Sean Gugger
(74) *Attorney, Agent, or Firm* — Crowell & Moring LLP (57) ABSTRACT

An energy supply system is provided with an electricity generating device for regeneratively generating electrical energy that can be fed into an electricity supply grid. The energy supply system includes an electricity generating device for regeneratively generating electrical energy which can be fed into an electricity supply grid, a hydrogen generating device for generating hydrogen using electrical energy from the regenerative electricity generating device, a methanation device for converting hydrogen generated by the hydrogen generating device and a supplied carbon oxide gas into a gas containing methane, and a gas providing device for providing a supplementary gas or a replacement gas in a variably specifiable supplementary/replacement gas quality suitable for feeding into a gas supply grid with the use of the gas containing methane from the methanation device and/or the hydrogen from the hydrogen generating device. A method of operating the system is also provided.

17 Claims, 4 Drawing Sheets (51) Int. Cl.
*C10L 3/08* (2006.01)
*C12M 1/107* (2006.01)
*C12M 1/00* (2006.01)

(56) References Cited

U.S. PATENT DOCUMENTS

| | | | | |
|---|---|---|---|---|
| 2003/0168864 | A1* | 9/2003 | Heronemus et al. | 290/55 |
| 2008/0245660 | A1 | 10/2008 | Little et al. | |
| 2009/0173081 | A1* | 7/2009 | Wallace et al. | 60/801 |
| 2010/0018115 | A1* | 1/2010 | Wallace et al. | 48/77 |
| 2010/0051450 | A1 | 3/2010 | Murahara | |
| 2010/0121125 | A1* | 5/2010 | Hippo et al. | 585/733 |
| 2010/0158792 | A1* | 6/2010 | Drnevich et al. | 423/650 |

FOREIGN PATENT DOCUMENTS

| | | |
|---|---|---|
| DE | 10 2009 007 567 | 9/2009 |
| EP | 2 149 625 A1 | 2/2010 |
| WO | WO 2008/142995 A1 | 11/2008 |
| WO | WO 2009/019159 A2 | 2/2009 |
| WO | WO 2009019159 A2 * | 2/2009 |

OTHER PUBLICATIONS

German Search Report dated Nov. 4, 2009 with partial English translation (nine (9) pages).

International Search Report dated Jul. 15, 2010 with English translation (six (6) pages).

N. Hasegawa, et al. "Integrated Carbon Recycling System for Mitigation of $CO_2$ Emissions Utilizing Degraded Thermal Energy", Energy Conyers. Mgmt., 1996, pp. 1333-1338, vol. 37, Nos. 6-8.

M. Gassner et al., "Thermo-Economic Optimisation of the Integration of Electrolysis in Synthetic Natural Gas Production from Wood", Energy, 2008, pp. 189-198.

Werner Schnurnberger et al., "Advanced Electrolysis Technique for Hydrogen Production in Intermittent Operation" ("Fortgeschrittene Elektrolysetechiken zur Wasserstoffherstellung Im Intermittierenden Betrrieb"), Chemie Ingenieur Technik, 1995, pp. 1320-1323, vol. 67.

K. Hashimoto et al., „Global $CO_2$ Recycling—Novel Materials and Prospect for Prevention of Global Warming and Abundant Energy Supply, Materials Science and Engineering A267, 1999, pp. 200-206.

T. Yoshida et al., "Carbon Recycling System Through Methanation of $CO_2$ in Flue Gas in LNG Power Plant", Energy Conyers. Mgmt., 1997, Suppl. pp. S443-S448, vol. 38.

John Ralston et al., "Catalytic $CO_2$ Recycle (CCR™) Technology", Mega Symposium, Aug. 25, 2008 (Twelve (12) pages).

K. W. Harrison et al., "Renewable Hydrogen: Integration, Validation and Demonstration", National Renewable Energy Laboratory, Conference Paper NREL/CP-581-43114, Jul. 2008.

K. W. Harrison et al., "Characterizing Electrolyzer Performance for Use in Wind Energy Applications", National Renewable Energy Laboratory, 2006.

Third-Party Observation Art. 115 EPC, Concerned Patent Application EP 2 334 590 A1 on Feb. 6, 2012 (Three (3) pages).

* cited by examiner

ENERGY SUPPLY SYSTEM AND OPERATING METHOD

BACKGROUND AND SUMMARY OF THE INVENTION

The invention relates to an energy supply system with an electricity generating device for the regenerative generation of electrical energy that can be fed into an electricity supply grid, and to an operating method for such an energy supply system.

The use of renewable forms of energy such as wind power, solar energy and hydroelectric power is becoming more and more important for electricity generation. Electrical energy is typically delivered to multiple consumers via long-range, trans-regional and trans-nationally connected electricity supply grids, known as electricity grids for short. As electrical energy as such cannot be stored in significant quantities, the electrical power fed into the electricity grid must be adapted to the consumer-side power demand, the so-called load. It is known that the load fluctuates over time, in particular depending on the time of day, the day of the week or even the season. The load profile is classically divided into three ranges—base load, medium load and peak load—and appropriate electrical energy generators are used depending on the type in these three load ranges. Continuous synchronization of electricity generation and electricity consumption is required for a stable and reliable electricity supply. Any deviations that occur are compensated by so-called positive or negative balancing energy or balancing power. Positive balancing power is required when the normal amount of electricity provided lags too far behind the current electricity demand, in order to prevent an undesired lowering of the grid frequency and failure of the electricity supply caused thereby. Negative balancing power is required when unexpected excess electricity generation power occurs occasioning an unexpected rise in frequency. The problem exists with regenerative electricity generating devices that for certain types such as wind power and solar energy the energy generation power is not present at all times and cannot always be controlled in a certain way, but is subject to fluctuations, e.g. depending on the time of day and the weather, which can only be predicted to a limited degree.

Laid-open publication DE 10 2009 007 567 A1 discloses a method for producing methanol by recycling carbon dioxide from the waste gas of fossil fuel-fired power plants, combined heat and power plants or other emitters of $CO_2$, the $CO_2$ being subjected to a methanol synthesis with hydrogen which is preferably generated from an electrolysis with regeneratively obtained electrical energy, in particular in low load phases of an associated electricity grid. The synthesized methanol can be stored temporarily in a methanol store or conveyed as a fuel to a heat or electricity generating plant. An energy generating installation carrying out the method consists of a combined heat and power plant, a wind, hydroelectric and/or solar power plant, an electrolysis plant, a store for $CO_2$, $O_2$ and $H_2$, respectively, a methanol synthesizing plant, a methanol store and a control system to control these installation components for generating energy depending on the electricity demand in a manner that is optimized for the load.

Laid-open publication DE 43 32 789 A1 discloses a method for storing hydrogen energy by reacting hydrogen, obtained for example by using solar or nuclear energy, in the presence of carbon dioxide into methane or methanol which can then be used, for example, as a fuel for vehicles or combustion plants.

Laid-open publication DE 10 2004 030 717 A1 discloses a method and a device for converting and storing regeneratively obtained energy by converting it into chemical energy with the use of electrical energy and carbon dioxide, the chemical energy being released again as chemical and electrical energy depending on demand. For this purpose, a recirculation process is provided in which energy from a geothermal or regenerative source is converted into electrical energy which is supplied to a consumer and an electrolysis device. Some of the hydrogen obtained from the electrolysis is supplied to a consumer and some is subjected to a synthesis with $CO_2$ from a $CO_2$ store to form a hydrocarbon and an alcohol. The hydrocarbon, for example methane, is stored in an associated store and some of it is supplied to a consumer and some to a combustion heating process to which, on the other hand, oxygen from the electrolysis is supplied. Using a thermodynamic process, the combustion heating process generates electrical energy, some of which is supplied to the electrical consumer and some to the electrolysis process. $CO_2$ generated in the combustion heating process is stored in the same way as $CO_2$ which comes from a $CO_2$ recovery process which is fed with $CO_2$ from the hydrocarbon consumer.

Laid-open publication WO 2009/019159 A2 discloses an energy distribution method with which an electricity grid that distributes electricity or loads is to be operated in a stable manner, regeneratively generated energy being used at least in a significant proportion to generate hydrogen, carbon dioxide from other power plants or a final storage site being hydrogenated together with the hydrogen in a hydrogenation plant, and a gaseous combustible hydrocarbon so generated being recycled in a power plant for generating electricity, wherein carbon is circulated.

It is known for gas supply grids that a supplementary gas and/or a replacement gas can be added to the gas that is usually distributed in a supply area, the so-called base gas, such as natural gas.

Supplementary gases are understood to be gas mixtures which differ significantly from the base gas in their composition and burning characteristics but, when mixed with the base gas, have a similar burning behavior as the base gas, and which are allowed to be added to the base gas in limited quantities. Replacement gases are understood to be gas mixtures which, despite a composition which differs from that of the base gas and burning characteristics which may also differ, have a similar burning behavior as the base gas at the same gas pressure and can completely replace the base gas when necessary. So-called conditioning gases can additionally be added. For the corresponding definitions and classifications of supplementary gas, replacement gas and gases for conditioning, reference can be made to the relevant specialist literature, see for example DVGW Technische Regel Arbeitsblatt G260: Gasbeschaffenheit, Wirtschafts-und Verlagsgesellschaft Gas und Wasser mbH, Bonn, January 2000; DVGW Technische Regel Arbeitsblatt G262: Nutzung von Gasen aus regenerativen Quellen in der öffentlichen Gasversorgung, Wirtschafts-und Verlagsgesellschaft Gas und Wasser mbH, Bonn, November 2004; Gaswärme-Institut e.V. Essen et al: Analyse und Bewertung der Nutzungsmöglichkeiten von Biomasse, Volume 4, 2005; and the study published by the Fachagentur nachwachsende Rohstoffe e.V.: Einspeisung von Biogas in das Erdgasnetz, Leipzig, 2006, ISBN 3-00-018346-9, see in particular pages 68 to 70.

The technical problem which the invention addresses is the provision of an energy supply system of the type mentioned at the beginning and of an operating method suitable therefor, with which regeneratively generated electrical energy can be used in an optimal fashion in order to ensure a stable and reliable electricity supply with a high proportion of electricity from renewable forms of energy even when regenerative electricity generators are used which have a significantly fluctuating generating power, such as wind power and/or photovoltaic power plants.

The invention solves this problem by providing an energy supply system, and an associated operating method.

The energy supply system according to the invention contains, in addition to the regenerative electricity generating device, a hydrogen generating device which can generate hydrogen using the regeneratively generated electrical energy, and a methanation device which can convert the hydrogen generated into a gas containing methane in the presence of a supplied carbon oxide gas, preferably carbon dioxide, or a synthesis gas. Furthermore, the energy supply system contains a gas providing device by means of which a gas can be provided in the quality of a supplementary gas or a replacement gas which can be fed into a gas supply grid, with the use of the gas containing methane from the methanation device and/or the hydrogen from the hydrogen generating device. By means of these installation components, the energy supply system is characteristically capable of providing large quantities of a supplementary gas or replacement gas, which can be fed into a gas supply grid and stored there or used for another purpose, from regeneratively generated electrical energy. Installations known per se can be used for the said system components, such as an electrolysis unit for generating hydrogen and a conventional methanation reactor.

The gas providing device is specially designed so as to provide the gas in a variably specifiable supplementary/replacement gas quality, for which it has, if necessary, corresponding gas preparation means. As a result of this special design of the gas providing device, the gas can be prepared optimally as appropriate for the situation in the quality of a supplementary gas, in order to feed the latter, for example, in a limited quantity into a gas supply grid, or in the quality of a replacement gas, in order to feed the latter, for example, as a full-value replacement for the base gas into a gas supply grid. The preparation of gas in the quality of supplementary gas typically requires a lower energy usage than the preparation of a replacement gas. On the other hand there is no limitation on the feeding of the replacement gas into the gas supply grid as it may optionally completely replace the base gas. It is to be understood that the gas providing device including its associated control means can, as necessary, take the form of a stand-alone installation component or can be integrated wholly or partially into the methanation device and/or the hydrogen generating device and/or a central installation control system. In each case, the gas generated using regenerative electrical energy can thus very advantageously, depending on demand, be provided differently and variably as supplementary or replacement gas and used, for example, for feeding into a gas supply grid.

In an advantageous development of the invention, the energy supply system contains a gas-into-electricity conversion device which can generate electrical energy using gas from the gas supply grid. Suitable means for achieving this are, for example, a high-efficiency gas and steam power plant, called a GuD power plant for short, or another means for converting methane into electricity such as gas turbines or methane-fired block-type thermal power plants having gas Otto engines, or engines or fuel cells which are adapted for methane. The gas and steam power plant will be mentioned primarily below as representative for all options for the conversion of methane into electricity.

The energy supply system thus allows the shifting of regenerative fluctuating electricity generation and hence a greater possibility of using regenerative electricity generators having a generating capacity that fluctuates depending on the type, with the required grid stability of an electricity grid fed with this electricity being maintained. At periods when regeneratively generated electricity, for example from wind power and/or photovoltaic power plants cannot be fed into the electricity grid for grid stability reasons or other technical and commercial reasons, it can be used to generate hydrogen which is transformed with carbon oxide gas by means of methanation into a supplementary or replacement gas which can be fed into the gas supply grid, stored there and used, in particular also for reconversion into electricity at periods with a high residual load of the electricity grid, i.e. with a high difference between the power demand on the electricity grid and the power provided by the regenerative electricity generating device.

The invention thus very efficiently solves the problems of the impossibility of storing sufficiently high amounts of electrical energy, as are required for public electricity grids, of the power output by important regenerative electricity generators which fluctuates, for example, according to the time of day, the season and the weather, and the required grid stability of the electricity grid. The energy supply system according to the invention enables electricity and gas supply grids to be networked or connected, which allows a high loading of regenerative electricity generators by using the prevailing conventional gas storage capacities in the gas supply grid, and additionally can provide high-quality regenerative positive and negative balancing energy or stored regenerative electricity for the electricity grid by appropriate load and generation management.

In an advantageous embodiment of the invention, the electricity generating device comprises in particular one or more wind power plants and/or one or more photovoltaic power plants and/or one or more geothermal power plants and/or one or more biomass power plants and/or one or more hydroelectric power plants and/or one or more solar power plants. In the future, these types of installation will become increasingly important for supplying electrical energy. Their specific integration into the energy supply system according to the invention allows a high degree of utilization thereof with the electricity grid stability maintained despite the power output by some of these regenerative electricity generators fluctuating considerably over time and the demand for electricity which fluctuates over time.

In a development of the invention, the energy supply system has means for supplying carbon dioxide to the methanation device from a power plant outputting carbon dioxide. This allows carbon dioxide which occurs in a power plant to be used and integrated, via the methanation device, into the energy cycle of the energy supply system.

In a development of the invention, the energy supply system contains means for supplying a gas containing carbon dioxide to the methanation device from a biogas installation, such as biogas or carbon dioxide separated therefrom. As a result, the regenerative use of biomass from a conventional biogas plant can advantageously be integrated into the energy supply system according to the invention.

In a development of the invention, according to the invention means are provided for the transfer of heat from the methanation device to a biogas installation. In this way, waste heat from the methanation device can be used in the biogas installation.

In a development of the invention, means are provided for supplying a supplementary or replacement gas obtained from a biogas plant to the gas providing device or to the gas supply grid, i.e. the biogas plant in this case also directly contributes to the feeding of the gas supply grid.

In a further advantageous development of the invention, the energy supply system contains means for supplying a synthesis gas containing carbon oxide from a biomass gasification installation to the methanation device. The synthesis gas, together with the hydrogen, can be converted into the methane-containing supplementary or replacement gas through an appropriate design of the methanation device.

In a development of the invention, the energy supply system contains an ORC (organic Rankine cycle) unit or another heat utilization unit for generating electrical energy using waste heat from the methanation device so that this waste heat can be used directly to generate electricity.

In a development of the invention, the energy supply system comprises a fuel dispensing device by means of which corresponding vehicles can be supplied with hydrogen generated by the hydrogen generating device and/or with electrical energy generated by the regenerative electricity generating device and/or with supplementary or replacement gas delivered by the gas providing device, wherein all three or only some of these energy sources for refuelling vehicles can be provided at the fuel dispensing device depending on the application and needs.

In a development of the invention, the energy supply system comprises an electricity supply grid to which the regenerative electricity generating device and the hydrogen generating device and the gas-into-electricity conversion device are connected, and/or a gas supply grid to which the methanation device and the gas-into-electricity conversion device are connected. The electricity supply grid and/or the gas supply grid are thus integrated into the energy supply system according to the invention, preferably both of them specifically connected to each other. In an embodiment of this aspect of the invention, the energy supply device comprises a gas store connected to the gas supply grid. The gas store can hereby be a gas store known per se for this purpose which is capable of temporarily storing the substitute natural gas delivered by the methanation device with high capacity.

In a development of the invention, the energy supply system comprises a control device which is configured so that the power output of the hydrogen generating device and/or of the gas-into-electricity conversion device can be set variably depending on a time-dependent power demand on the electricity supply grid. This forms the basis for advantageous and efficient load and generation management of the system and in particular of the electricity supply grid.

In an embodiment of this aspect of the invention, the control device is designed so that, at periods when there is an increased demand on the electricity grid for power generation, a reduced power consumption of the hydrogen generating device and/or an increased feed-in power of the gas-into-electricity conversion device can be set and/or, at periods when there is a reduced demand for power generation, the power consumption of the hydrogen generating device can be increased and/or the feed-in power of the gas-into-electricity conversion device can be reduced. In other words, the control device can provide positive and negative balancing energy to ensure grid stability of the electricity grid using the regeneratively generated electrical energy temporarily stored in reconvertible fashion in the gas supply grid as hydrogen and/or a substitute natural gas. This is made possible by operating the system using the method according to the invention.

In another embodiment of this aspect of the invention, the control device is designed so that the power of the hydrogen generating device and/or of the gas-into-electricity conversion device can be set depending on a projected power demand profile of the electricity supply grid and/or a projected electricity generating power profile of the regenerative electricity generating device. This design of the control device allows the energy supply system to operate in a forward-looking manner from the point of view of the required electricity grid stability and taking into consideration the power, which may fluctuate, provided by the regenerative electricity generating device and the fluctuating electricity demand. To do this, the energy supply system can be operated using the operating method according to the invention in a corresponding further development.

In a development of the invention, the supplementary or replacement gas is provided selectively in one of multiple specifiable quality levels. This allows optimal adaptation of the operation of the methanation device and/or of the hydrogen generating device to requirements which can, for example, be set for the supplementary/replacement gas by the gas supply grid. When allowed by the gas supply grid, a supplementary gas of a lower quality level can be provided at lower cost, and when there are higher requirements a supplementary or replacement gas of a higher quality level can be provided at typically a slightly higher cost.

Advantageous embodiments of the invention are described below and illustrated in the drawings.

DETAILED DESCRIPTION OF THE DRAWINGS

Figure 1:
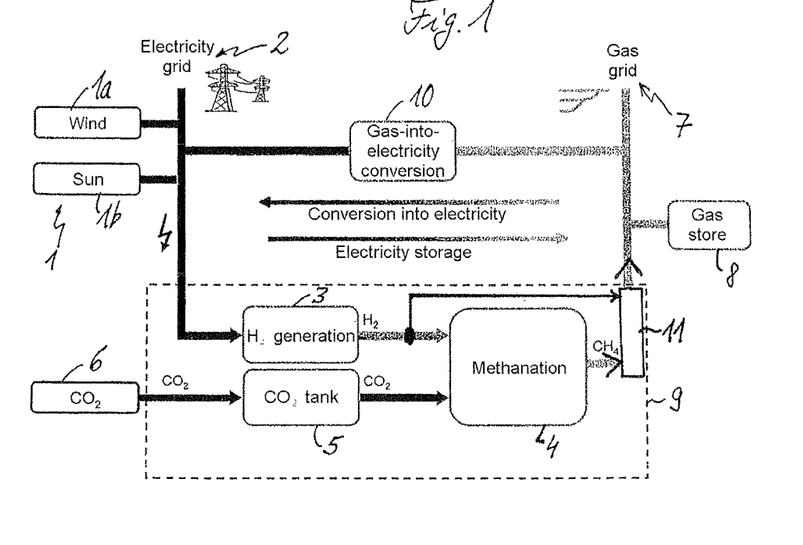
FIG. 1 shows a schematic block diagram of an energy supply system with regenerative electricity generators, a hydrogen generating device, a methanation device and a gas-into-electricity conversion device with corresponding connection to an electricity supply grid and a gas supply grid.

FIG. 1 shows schematically an energy supply system which allows regeneratively generated electrical energy to be stored as supplementary or replacement gas with reconversion to electricity as necessary. The energy supply system contains a regenerative electricity generating device 1 which in the example shown comprises wind power plants 1a and photovoltaic power plants 1b and generates electrical energy from renewable forms of energy for feeding into an electricity grid 2, in particular a public electricity grid. Furthermore, the energy supply system contains a hydrogen generating device 3 connected to the electricity grid 2 as a consumer and a methanation device 4 connected downstream therefrom which converts the hydrogen generated in the hydrogen generating device 3 using electrical energy from the electricity grid 2, together with supplied carbon oxide gas, for example carbon dioxide ($CO_2$), into methane gas or a methane-rich gas. The carbon dioxide comes from a carbon dioxide tank 5 which is fed by a carbon dioxide source 6. The gas generated by the methanation device 4 is used by a gas providing device 11 to provide a supplementary or replacement gas with a specifiable gas quality and to feed it into a gas supply grid 7, gas grid for short, to which a gas store 8 is connected. Optionally, a certain part of the hydrogen ($H_2$) generated by the hydrogen generating device 3 can also be supplied directly to the gas providing device 11, bypassing the methanation device 4, to provide the supplementary or replacement gas.

The hydrogen generating device 3, the methanation device 4, the $CO_2$ tank 5 and the gas providing device 11 thus form an electricity-converting system part 9 which converts electricity from the electricity grid 2, and in particular electricity from the regenerative electricity generating device 1, into a supplementary or replacement gas which can easily be stored in large quantities in the gas grid 7, where the gas grid is in particular a conventional gas grid with gas storage capacities known per se. In an inverse arrangement to the system part 9, the energy supply system contains a gas-into-electricity conversion device 10 for converting gas removed from the gas grid into electricity and feeding the electrical energy generated thereby into the electricity grid 2. In particular, the supplementary or replacement gas obtained using the regeneratively generated electrical energy can thereby be reconverted into electricity. The electricity-converting system part 9 can hereby be installed so that it is physically separate from the gas store 8 and from the gas-into-electricity conversion device 10 as well as from the $CO_2$ source 6.

Figure 2:
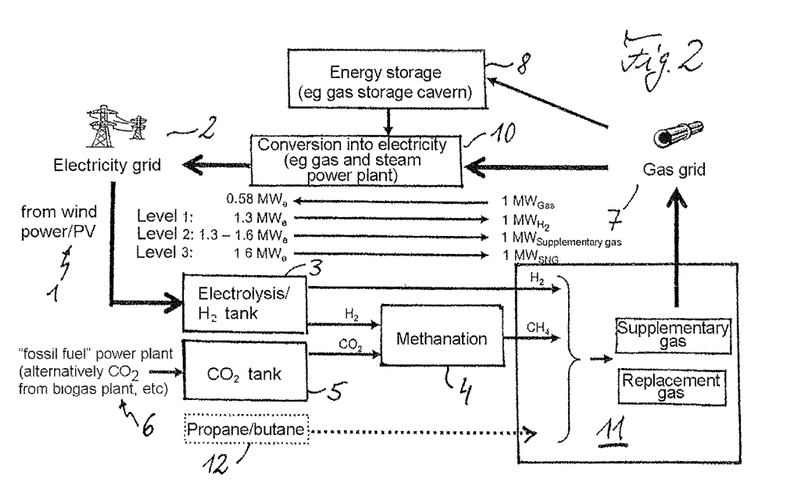
FIG. 2 shows a block diagram similar to FIG. 1 with a more detailed view of possible operating alternatives.

FIG. 2 illustrates in rather more detail some possible alternatives for realizing such an energy supply system and operating said system. As indicated, the hydrogen generating device 3 can be formed, for example, by a conventionally constructed electrolysis unit and a connected hydrogen tank. A biogas plant or a power plant for converting a fossil-fuel energy source into electricity which emits $CO_2$ may be considered as representative as a possible source 6 of $CO_2$. The gas-into-electricity conversion device 10 can, for example, take the form of a gas and steam power plant or a block-type thermal power station, BHKW for short. The gas store 8 can contain, for example, conventional geological pore and/or cavern storage facilities.

Through a corresponding design of the gas providing device 11, supplementary or replacement gas can, as required, be provided variably or selectively in different gas qualities using the hydrogen generated in the hydrogen generating device 3 and/or the methane-containing gas generated in the methanation device 4 and fed into the gas grid 7. In an exemplary embodiment illustrated in FIG. 2, it is provided that supplementary/replacement gas can be provided selectively in one of three different gas qualities. At a first level, it is provided that virtually pure hydrogen from the hydrogen generating device 3 is added as a supplementary gas to the base gas of the gas grid in such a way that, beyond a corresponding gas mixture point, a gas which can still be fed in, regarding its quality, results which fulfils the prescribed feed-in guidelines for the gas grid 7. For a hydrogen generating power of 1 MW, when a highly efficient electrolysis is used, approximately 1.3 MW of electrical power is needed. At a second level, a supplementary gas is fed in which, in addition to a proportion of hydrogen that is still as high as possible, contains a small proportion of methane from the methanation device 4 such that, after the gas mixture point, a gas again results which fulfils the feed-in guidelines. The proportion of hydrogen can be supplied directly to the gas providing device 11 by the hydrogen generating device 3 and/or via the methanation device 4. The latter can be achieved by the hydrogen from the hydrogen generating device 3 being guided through the methanation device 4 in such a way, and the operation of the methanation device 4 being set in such a way, that the methanation device 4 converts only part of the supplied hydrogen into methane and outputs the remaining supplied hydrogen together with the methane generated. Approximately 1.3 MW to 1.6 MW of electrical power are needed to obtain 1 MW of power from such a supplementary gas. At a third level, a replacement gas, also termed a substitute natural gas, is fed in, for which the proportion of hydrogen in the replacement gas is limited to less than 5% by volume and the proportion of $CO_2$ is limited to less than 6% by volume. Approximately 1.6 MW of electrical power are needed for 1 MW of power from such a substitute natural gas (SNG). 1.6 MW of electrical power here corresponds to approximately 0.2 tonnes per hour of carbon dioxide which needs to be supplied to the methanation device 4.

Depending on the application and demand, each of the three levels can be modified or split up such that, in addition to the supplementary/replacement gas, a conditioning gas is optionally added, for example to set desired burning characteristics for the gas beyond the feed-in point. The conventional conditioning gases can be used for this, in particular $C_{2-4}$ hydrocarbons such as propane and/or butane, specifically for example LPG (liquefied petroleum gas) and/or DME (dimethyl ether), which are supplied from a corresponding hydrocarbon source 12, air and/or nitrogen. Further refinement of the quality levels can, when necessary, be provided by specific quantitative settings for the proportion of hydrogen or methane which needs to be added. For each quality level, the cost of the energy to provide the corresponding gas increases, but so does the quality of the gas. Whereas supplementary gas generally can only be added to the base gas in the gas grid in a limited quantity, replacement gas is suitable as substitute natural gas for an equivalent use to the base gas, and, in contrast with the supplementary gas, the gas grid provider is usually even obliged to accept replacement gas for feeding into his gas grid.

It should be understood that the gas providing device 11 is equipped with the components required for the variable provision of the supplementary/replacement gas in different gas qualities, including corresponding control means which suitably adjust the addition of the different gas constituents and, if necessary, also the operation of the installation components delivering these gas constituents by a corresponding closed-loop control or open-loop control. In particular, the gas providing device 11 has corresponding means for detecting the composition of the base gas already present in the gas grid, or this information is supplied to it, so that it can decide the gas quality to be set for the supplementary/replacement gas. Alternatively, the information on the supplementary/replacement gas quality that is desired at the current time in each case can be supplied to it from outside.

With the explained system design, a comparatively high electricity storage efficiency can be achieved which, depending on requirements for the gas conditioning, is between approximately 35% and 45%. The present system allows significantly improved utilization of the potential of wind energy and other types of regenerative electricity generation, it being possible for high-quality balancing energy for the electricity grid to be provided extremely quickly by the hydrogen generating device 3 and the gas-into-electricity conversion device 10 being controlled in a corresponding fashion depending on the power demand on the electricity grid 2. The feeding of generated supplementary/replacement gas into an existing gas grid allows conversion into electricity independently of location without the problem of local hydrogen storage. In addition to these electricity storage and electricity load regulation functionalities, this energy supply system offers the additional advantage of using carbon dioxide that occurs elsewhere and would otherwise remain unused.

Some advantageous alternative embodiments of the energy supply system are explained in more detail below with reference to FIGS. 3 to 8, in which the same reference numerals have in each case been used for identical or functionally equivalent components, for the sake of clarity.

Figure 3:
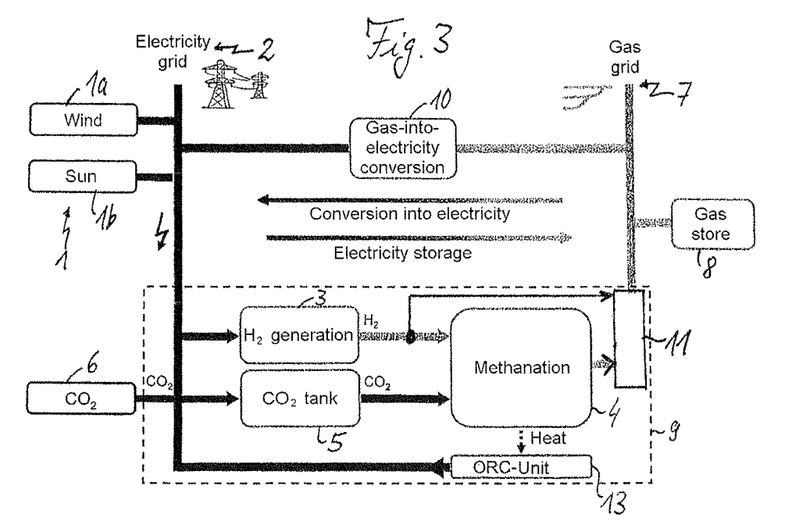
FIG. 3 shows a block diagram similar to FIG. 1 for an alternative with an ORC unit.

The alternative system shown in FIG. 3 contains, in addition to the basic components in FIG. 1, an ORC unit 13 in which waste heat from the methanation device 4 is used to generate additional electrical energy which is fed into the electricity grid 2. Alternatively, another conventional heat utilization plant can serve this purpose instead of the ORC unit 13.

Figure 4:
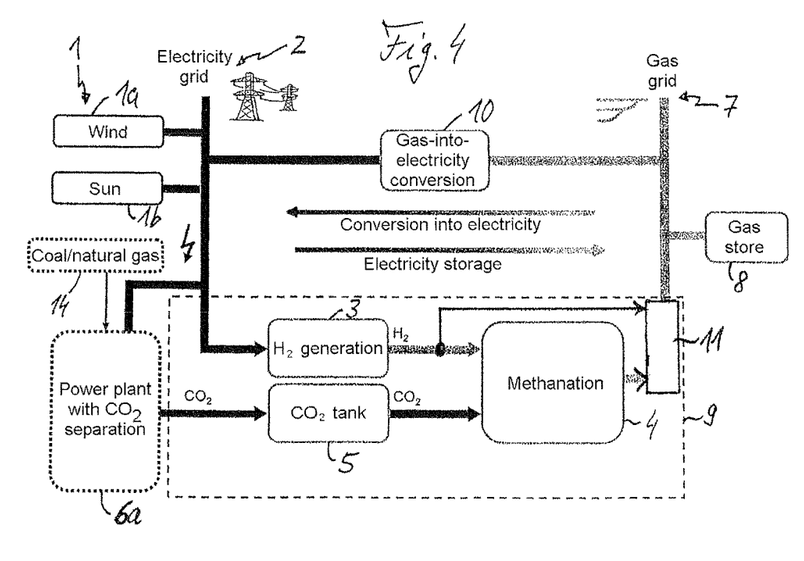
FIG. 4 shows a block diagram similar to FIG. 1 for an alternative with the use of carbon dioxide from a power plant for the conversion of fossil energy sources into electricity.

The alternative system shown in FIG. 4 uses for the source of carbon dioxide a conventional power plant 6a which generates electrical energy by converting a fossil-fuel energy source 14, such as coal and/or natural gas, into electricity and feeds it into the electricity grid 2, and comprises a $CO_2$ separation. The separated $CO_2$ is temporarily stored in the $CO_2$ tank 5.

The power plant delivering $CO_2$ can, for example, be a so-called "carbon capture" type. The carbon dioxide can, for example, be transported from the power plant 6a to the $CO_2$ tank 5 in liquefied form via a pipeline or by road, rail or ship.

Figure 5:
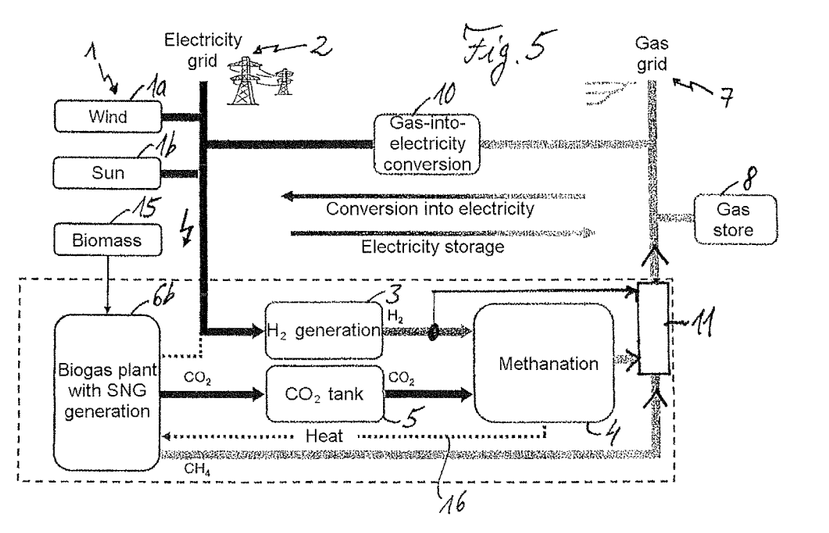
FIG. 5 shows a block diagram similar to FIG. 1 for an alternative with the use of separated carbon dioxide from a biogas plant.

The alternative system shown in FIG. 5 uses for the source of $CO_2$ a biogas plant 6b which is designed to generate a biogas from supplied biomass and to separate $CO_2$ from the biogas generated. As a result of the separation of $CO_2$, a methane-containing supplementary gas or replacement gas which can be fed in is obtained from the biogas, is supplied by the biogas plant 6b to the gas providing device 11 or, in the last-mentioned case, can also be fed as substitute natural gas directly into the gas grid 7. Waste heat from the methanation device 4 can be transported to the biogas plant 6b via an optional heat transport path 16 so that it can be used there. Alternatively, this waste heat can also be used elsewhere, for example fed into a heating grid.

Figure 6:
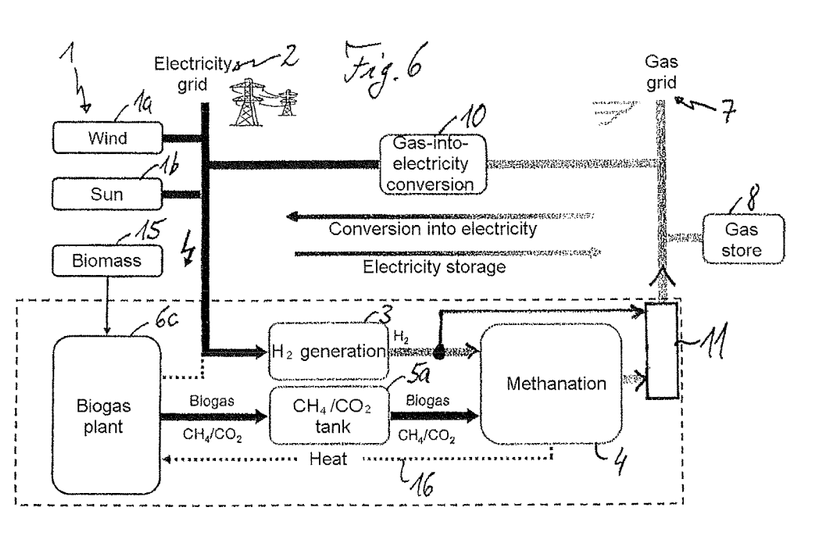
FIG. 6 shows a block diagram similar to FIG. 1 for an alternative with the use of a biogas from a biogas plant as a source of carbon dioxide for the methanation.

The alternative system shown in FIG. 6 uses for the source of $CO_2$ a biogas plant 6c like the alternative system in FIG. 5, but in this case without the separation of $CO_2$ from the biogas generated. The biogas containing $CO_2$ is temporarily stored in a corresponding biogas tank 5a which here functions as a carbon dioxide tank and is supplied from the latter to the methanation device 4. The methanation device 4 is in this case suitably designed for converting the biogas in the presence of hydrogen, in order to generate the desired supplementary/replacement gas.

Figure 7:
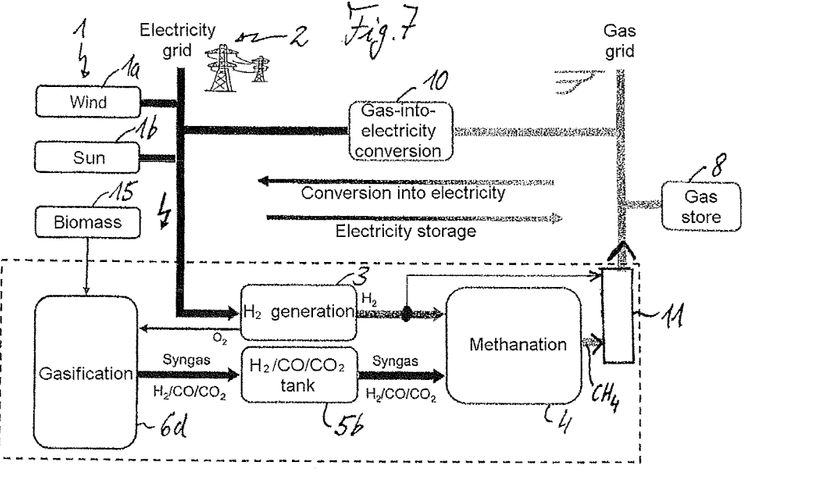
FIG. 7 shows a block diagram similar to FIG. 1 for an alternative with the use of a synthesis gas from a biomass gasification reactor as a source of carbon dioxide.

The alternative system shown in FIG. 7 contains a conventional gasification reactor 6d for gasifying biomass 15, in which oxygen obtained in the hydrogen generating device 3 by the electrolysis process can be supplied to the gasification reactor 6d. The oxygen can be used there for autothermal process management of the gasification reaction. The synthesis gas which contains carbon oxide and is generated by the gasification reactor 6d is temporarily stored in a corresponding synthesis gas tank 5b and supplied from there to the methanation device 4, if necessary after corresponding gas cleaning. The methanation device 4 is in this case designed to convert into methane both the carbon dioxide and the carbon monoxide which are contained in the synthesis gas in addition to hydrogen, the hydrogen from the hydrogen generating device 3 being used in addition.

Figure 8:
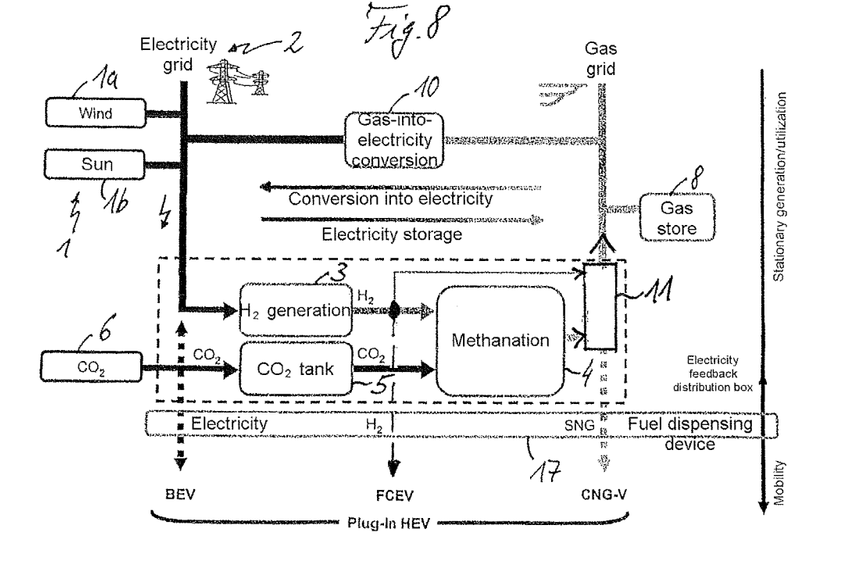
FIG. 8 shows a block diagram similar to FIG. 1 for an alternative with an additional fuel dispensing device for fuelling vehicles with hydrogen, electrical energy and/or a substitute natural gas.

FIG. 8 illustrates an alternative system which is additionally equipped with a fuel dispensing device 17 which makes it possible to refuel a vehicle with a choice of electrical energy, hydrogen or supplementary gas, preferably substitute natural gas. Battery electric vehicles (BEV) can thus be charged up at a corresponding electricity connection point which is connected to the electricity grid 2. Hydrogen-powered vehicles, for example fuel cell electric vehicles (FCEV) can be refuelled at a hydrogen connection point, and compressed natural gas vehicles (CNG-V) can be refuelled with substitute natural gas at a gas connection point. Alternatively, the gas providing device can in this case also be designed to provide a vehicle fuel gas corresponding to DIN standard 51624 with a gas quality which exceeds the minimum quality of the replacement gas. This includes the possibility of providing an $H_2/CH_4$ fuel gas known as "hythane". In each case, all three types of energy refuelling can be traced back to regeneratively generated electrical energy, i.e. the vehicles are fed entirely with renewable forms of energy. Hybrid electric vehicles, which can be operated using more than one of these three sources of energy, can also be refuelled via a corresponding combination connection point (plug-in HEV).

It should be understood that the components mentioned in each case for the individual alternative systems shown in FIGS. 3 to 8 can be combined in any manner. Thus, for example, the ORC unit 13 from FIG. 3 can also be installed in the other alternative systems and, instead of just one source of carbon oxide, in corresponding further alternative systems several of the sources of carbon oxide 6, 6a to 6d mentioned can be provided in parallel.

The methanation device 4 is designed for the respective optimal conversion of the supplied carbon oxide gas with the supplied hydrogen. With the exception of the alternative system in FIG. 7, $CO_2$ is supplied as the carbon oxide gas. In these cases, the conversion takes place using the overall highly exothermic carbon dioxide hydrogenation reaction This is connected with the CO methanation reaction by the endothermic reverse shift reaction Such a methanation of a gas consisting predominantly of $CO_2$ without a higher CO proportion requires a suitable process management and reactor design. In the case of the use of a biomass gasification reactor, as in the alternative system in FIG. 7, the methanation device 4 is designed for the methanation of the generated synthesis gas.

In all of the alternatives mentioned, the energy supply system contains a control device for open-loop or closed-loop controlling the overall system, which can be implemented in a per se conventional manner as a system or installation control and is therefore not shown in detail here and is explained below only in terms of its characteristic open-loop/closed-loop control functionalities which are of interest here.

The system control implemented in the control device is based initially on conventional electricity grid control measures, such as the division into base load, medium load and peak load of the electricity grid 2. In addition, the regenerative electricity generators are divided into fluctuating types, such as wind power plants and photovoltaic power plants, and controllable types, such as biogas plants, hydroelectric power stations, geothermal power plants and marine energy power plants. So-called balancing power or power reserve is necessary for stable operation of the electricity grid 2, in order to compensate for unexpected imbalances between the demand and generation of electrical energy and thus to keep the grid frequency in each case within a predetermined tolerance range. Positive balancing power is needed when the electricity generating power falls unexpectedly and/or the load, i.e. power consumption, rises unexpectedly. Negative balancing power is needed, for example, when high-power consumers fail for a short period of time. The demand for balancing power increases as the proportion of regenerative electricity generators with a fluctuating electricity supply increases.

The control device designed for the present energy supply system first calculates in anticipation the so-called residual load as the electricity demand which it is anticipated cannot be covered by the fluctuating regenerative electricity generators such as wind power plants and photovoltaic power plants. Standardized load profiles of the electricity demand which is to be expected, on the one hand, and a prediction of the feed-in power which is to be expected for the regenerative electricity generating device, for example taking weather data into consideration, can be used for this forecast. The residual load is divided over the course of the day into different time zones with periods of high residual load, low residual load and medium residual load. At the periods with low residual load, the control device controls the relevant system components such that regeneratively generated electrical energy is stored as substitute natural gas, i.e. the hydrogen generating device 3 and the methanation device 4 are activated or their generating power is increased. At periods of high residual load, the hydrogen generating device 3 and the methanation device 4 remain deactivated or in a reduced-output state, and the gas-into-electricity conversion device 10 is activated in order to reconvert temporarily stored substitute natural gas into electricity and hence in addition to provide electrical energy. In intervening periods, depending on demand and the application, the regeneratively generated electrical energy can be used directly or, with partial loading of the hydrogen generating device 3 and the methanation device 4, be partially used to generate substitute natural gas. Using these open-loop and closed-loop control, i.e. regulating, measures, the fluctuations in the residual load depending on the time of day can be significantly reduced and hence the feed-in from fluctuating regenerative electricity generators can be stabilized. These measures ensure that the grid stability and supply reliability of the electricity grid 2 are not affected by the increasing use of fluctuating regenerative electrical energy generators.

The gas-into-electricity conversion device 10 is activated to provide positive balancing power. Alternatively or additionally, the hydrogen generating device 3 is temporarily switched off or is operated with reduced output. Power consumption of the hydrogen generating device 3 is increased to provide negative balancing power.

The electricity-converting system part 9 can be operated in different ways according to demand and the application. One option consists in converting a certain part of the regeneratively generated electrical energy permanently into substitute natural gas. Another option consists in a block operation, in which the hydrogen generating device is active only at periods of low residual load. In continuous operation, part of the output of the regenerative electricity generators is held in reserve to generate hydrogen. The continuously generated substitute natural gas can be removed from the gas grid 7 as balancing energy, and both positive and negative balancing energy can be provided within seconds. This supports a high utilization of the methanation device 4 and hence a high economic efficiency of the overall system. In block operation, for example in the case of a wind power plant when there are high wind levels and a low electricity demand, the excess wind energy can be converted into substitute natural gas and temporarily stored in the gas grid 7. During periods of low wind levels and high electricity demand, the energy temporarily stored in this way can be reconverted into electricity.

As can be seen from the above embodiments, the energy supply system according to the invention enables the interconnection of an electricity grid and a gas grid with the possibility of storing high quantities of regeneratively generated electrical energy in the form of substitute natural gas in the gas grid. Electricity storage efficiency of up to approximately 45% can thus be achieved. Carbon dioxide which is otherwise unused can be used as a further option. The energy supply system can operate in such a way that, despite the increasing use of regenerative electricity generators with a significantly fluctuating power output, the grid stability and supply reliability of the electricity grid are not affected.

In an alternative to the above embodiments, the energy supply system according to the invention is also suitable, as required, for generating just methane. The regeneratively synthesized methane in this case is supplied for a different use, instead of reconversion into electricity, so that the gas-into-electricity conversion device is then not absolutely necessary. In this alternative embodiment, the system is suitable, for example as a stand-alone system, for generating just methane in remote regions.

As the above explanations make also clear, the invention enables the use of not only hydrogen and $CO_2$ but also of a methane-containing gas obtained by methanation and a CO-containing gas obtained, for example, by biomass gasification as an input gases for providing a gas with a gas quality that qualifies it as a supplementary/replacement gas which can be fed into a gas grid. The supplementary/replacement gas can be provided in a $CO_2$-neutral way, wherein the $CO_2$ can come in particular from the air, a biogas and/or a biomass gasification gas. In order to provide balancing power or to hold balancing power in reserve, intermittent or closed-loop controlled operation of the electrolysis process is possible, wherein the methanation process does not need to take place intermittently on the same scale, which has advantages in terms of the lifetime and profitability of the methanation process. Because gas can be stored temporarily and an intelligent control design is possible, decoupling can be obtained of a typically shorter electrolysis time, for example less than 2000 h/year, from a typically longer methanation time, for example up to approximately 8760 h/year. To operationally manage the overall system according to demand, weather data and weather forecasts can when necessary be taken into consideration in order to estimate the capacity for regenerative electricity generation which can be expected.

The invention claimed is:
1. An energy supply system, comprising:
an electricity generating device for regeneratively generating electrical energy feedable into an electricity supply grid;
a hydrogen generating device for generating hydrogen using electrical energy from the regenerative electricity generating device;
a methanation device for converting hydrogen generated by the hydrogen generating device and a supplied carbon oxide gas into a gas containing methane; and
a gas providing device for providing one of a supplementary gas and a replacement gas in a variably specifiable supplementary/replacement gas quality suitable for feeding into a gas supply grid with the use of at least one of the gas containing methane from the methanation device and the hydrogen from the hydrogen generating device, wherein the one of the supplementary gas and the replacement gas is added to the gas supply grid when the regeneratively generated electrical energy cannot be fed into the electricity supply grid, the gas providing device is operatively configured to provide the one of the supplementary gas or replacement gas selectively in a plurality of predetermined quality levels, said plurality of predetermined quality levels comprises at least:

a first level where virtually pure hydrogen is added as a supplementary gas, a second level where a supplementary gas is added containing some methane in addition to hydrogen, and a third level where a replacement gas is added containing an enhanced amount of methane and a decreased amount of hydrogen as compared to the second level, said decreased hydrogen amount is less than 5% by volume, and the gas providing device is configured to alternatingly switch between each of the first, second, and third level.

2. The energy supply system as claimed in claim 1, further comprising:

a gas-into-electricity conversion device for generating electrical energy using gas from a gas supply grid.

3. The energy supply system as claimed in claim 1, wherein the regenerative electricity generating device comprises at least one of:

one or more wind power plants, one or more photovoltaic power plants, one or more geothermal power plants, one or more biomass power plants, and one or more hydroelectric power plants and one or more solar power plants.

4. The energy supply system as claimed in claim 3, further comprising at least one of:

means for supplying carbon dioxide to the methanation device from a power plant outputting carbon dioxide;

means for supplying a gas containing carbon oxide to the methanation device from a biogas plant;

means for supplying a synthesis gas containing carbon oxide from a biomass gasification installation to the methanation device;

means for the transfer of heat from the methanation device to the biogas plant; and means for supplying a supplementary or replacement gas obtained from the biogas plant to the gas providing device or to the gas supply grid.

5. The energy supply system as claimed in claim 3, further comprising at least one of:

an ORC unit or other heat utilization installation for generating electrical energy using waste heat from the methanation device;

a fuel dispensing device for supplying vehicles with at least one of hydrogen generated by the hydrogen generating device, electrical energy generated by the regenerative electricity generating device, and supplementary or replacement gas provided by the gas providing device.

6. The energy supply system as claimed in claim 5, further comprising at least one of:

an electricity supply grid to which the regenerative electricity generating device, the hydrogen generating device and the gas-into-electricity conversion device are connected; and a gas supply grid to which the gas providing device and the gas-into-electricity conversion device are connected.

7. The energy supply system as claimed in claim 6, further comprising:

a gas storage which is connected to the gas supply grid.

8. The energy supply system as claimed in claim 6, further comprising:

a control device which is configured to variably set at least one of the power need of the hydrogen generating device and the feed-in power of the gas-into-electricity conversion device depending on a time-dependent power demand on the electricity grid.

9. The energy supply system as claimed in claim 8, wherein, at least one of:

(a) the control device is at least one of operatively configured to (i) set at least one of a reduced power need of the hydrogen generating device and an increased feed-in power of the gas-into-electricity conversion device at periods when there is an increased demand on the electricity grid for power generation, and (ii) set at least one of an increased power need of the hydrogen generating device and a reduced feed-in power of the gas-into-electricity conversion device at periods when there is a reduced demand on the electricity grid for power generation; and (b) the control device is designed to set at least one of the power need of the hydrogen generating device and the feed-in power of the gas-into-electricity conversion device depending on at least one of a projected power demand profile of the electricity supply grid and a projected electricity generating power profile of the regenerative electricity generating device.

10. A method for operating an energy supply system that comprises an electricity generating device for regeneratively generating electrical energy feedable into an electricity supply grid, a hydrogen generating device for generating hydrogen using electrical energy from the regenerative electricity generating device, a methanation device for converting hydrogen generated by the hydrogen generating device and a supplied carbon oxide gas into a gas containing methane, and a gas providing device, the method comprising the act of:

providing a supplementary gas or replacement gas in a variably specifiable supplementary/replacement gas quality suitable for feeding into a gas supply grid using at least one of the gas containing methane from the methanation device and the hydrogen from the hydrogen generating device, wherein the supplementary gas or the replacement gas is provided to the gas supply grid when the regeneratively generated electrical energy cannot be fed into the electricity supply grid, the supplementary or replacement gas is provided selectively in one of a plurality of predetermined quality levels, said plurality of predetermined quality levels comprises at least:

a first level where virtually pure hydrogen is added as a supplementary gas, a second level where a supplementary gas is added containing some methane in addition to hydrogen, and a third level where a replacement gas is added containing an enhanced amount of methane and a decreased amount of hydrogen as compared to the second level, said decreased hydrogen amount is less than 5% by volume, and the gas providing device is configured to alternatingly switch between each of the first, second, and third level.

11. The method as claimed in claim 10, further comprising at least one of the acts of:
setting at least one of a reduced power consumption of the hydrogen generating device and an increased feed-in power of the gas-into-electricity conversion device at periods when there is an increased demand on the electricity grid for power; and
setting at least one of an increased power consumption of the hydrogen generating device and a reduced feed-in power of the gas-into-electricity conversion device at periods when there is a reduced demand on the electricity grid for power.

12. The method as claimed in claim 11, wherein at least one of the power consumption of the hydrogen generating device and the feed-in power of the gas-into-electricity conversion device is set depending on at least one of a projected power demand profile of the electricity supply grid and a projected electricity generating power profile of the electricity generating device.

13. The method as claimed in claim 10, further comprising the act of:
variably setting at least one of the power consumption of the hydrogen generating device and the feed-in power of the gas-into-electricity conversion device depending on a time-dependent power demand on the electricity supply grid.

14. The energy supply system as claimed in claim 1, wherein the gas providing device comprises a corresponding control device configured to adjust addition of the methane from the methanation device and the hydrogen from the hydrogen generating device to achieve the desired variably specifiable supplementary/replacement gas quality.

15. The method as claimed in claim 10, further comprising the act of:
adjusting addition of the methane from the methanation device and the hydrogen from the hydrogen generating device, using a corresponding control device, to achieve the desired variably specifiable supplementary/replacement gas quality.

16. An energy supply system, comprising:
an electricity generating device for regeneratively generating electrical energy feedable into an electricity supply grid;
a hydrogen generating device for generating hydrogen using electrical energy from the regenerative electricity generating device;
a methanation device for converting hydrogen generated by the hydrogen generating device and a supplied carbon oxide gas into a gas containing methane; and
a gas providing device for providing one of a supplementary gas and a replacement gas in a variably specifiable supplementary/replacement gas quality suitable for feeding into a gas supply grid with the use of at least one of the gas containing methane from the methanation device and the hydrogen from the hydrogen generating device, wherein
the gas providing device is operatively configured to provide the supplementary gas or replacement gas selectively in a plurality of predetermined quality levels,
said plurality of predetermined quality levels comprises at least:
a first level where virtually pure hydrogen is added as a supplementary gas,
a second level where a supplementary gas is added containing some methane in addition to hydrogen, and
a third level where a replacement gas is added containing an enhanced amount of methane and a decreased amount of hydrogen as compared to the second level,
said decreased hydrogen amount is less than 5% by volume, and the gas providing device is configured to alternatingly switch between each of the first, second, and third level.

17. A method for operating an energy supply system that comprises an electricity generating device for regeneratively generating electrical energy feedable into an electricity supply grid, a hydrogen generating device for generating hydrogen using electrical energy from the regenerative electricity generating device, a methanation device for converting hydrogen generated by the hydrogen generating device and a supplied carbon oxide gas into a gas containing methane, and a gas providing device, the method comprising the act of:
providing a supplementary gas or replacement gas in a variably specifiable supplementary/replacement gas quality suitable for feeding into a gas supply grid using at least one of the gas containing methane from the methanation device and the hydrogen from the hydrogen generating device, wherein
the supplementary or replacement gas is provided selectively in a plurality of predetermined quality levels,
said plurality of predetermined quality levels comprises at least:
a first level where virtually pure hydrogen is added as a supplementary gas,
a second level where a supplementary gas is added containing some methane in addition to hydrogen, and
a third level where a replacement gas is added containing an enhanced amount of methane and a decreased amount of hydrogen as compared to the second level,
said decreased hydrogen amount is less than 5% by volume, and
the gas providing device is configured to alternatingly switch between each of the first, second, and third level.

* * * * *